US008377047B2

(12) United States Patent
Dai

(10) Patent No.: US 8,377,047 B2
(45) Date of Patent: Feb. 19, 2013

(54) SYSTEMS AND METHODS FOR FINE-TUNING REFRACTIVE SURGERY

(75) Inventor: Guang-Ming Dai, Fremont, CA (US)

(73) Assignee: AMO Development, LLC., Santa Ana, CA (US)

(*) Notice: Subject to any disclaimer, the term of this patent is extended or adjusted under 35 U.S.C. 154(b) by 1050 days.

(21) Appl. No.: 12/178,127

(22) Filed: Jul. 23, 2008

(65) Prior Publication Data
US 2009/0036879 A1 Feb. 5, 2009

Related U.S. Application Data

(60) Provisional application No. 60/953,425, filed on Aug. 1, 2007.

(51) Int. Cl.
*A61B 18/18* (2006.01)
*A61B 19/00* (2006.01)
(52) U.S. Cl. ............... 606/4; 606/5; 606/6; 128/898
(58) Field of Classification Search ............... 606/1–19, 606/166; 607/88–94; 128/898
See application file for complete search history.

(56) References Cited

U.S. PATENT DOCUMENTS

| 6,478,792 B1 | 11/2002 | Haensel |
| 2005/0171515 A1* | 8/2005 | Chernyak ............... 606/5 |
| 2007/0038202 A1* | 2/2007 | Celestino et al. ............ 606/10 |
| 2008/0058781 A1 | 3/2008 | Langeweyde et al. |
| 2010/0114077 A1 | 5/2010 | Dai |

FOREIGN PATENT DOCUMENTS

| DE | 10 2004 033819 A1 | 2/2006 |
| WO | WO 03/051189 A | 6/2003 |
| WO | WO 2006/087180 A | 8/2006 |
| WO | WO 2009/018157 A2 | 2/2009 |

OTHER PUBLICATIONS

PCT International Search Report and Written Opinion mailed Mar. 2, 2011; International Application No. PCT/US2010/058383, 11 pages.
PCT International Search Report and Written Opinion mailed Mar. 24, 2009; International Application No. PCT/US2008/071212, 19 pages.
Dubbelman, M. et al., "The shape of the aging human lens: curvature, equivalent refractive index and the lens paradox," Vision Research 41 (2001), pp. 1867-1877.
Garner, Leon, et al., "Radius of curvature of the posterior surface of the cornea,"Optometry and Vision Science, vol. 74, No. 7, Jul. 1997, pp. 496-498.
Roberts, Cynthia, "The cornea is not a piece of plastic,"Journal of Refractive Surgery, vol. 16, Jul./Aug 200, pp. 407-413.

* cited by examiner

*Primary Examiner* — Ahmed Farah
*Assistant Examiner* — William Cheng
(74) *Attorney, Agent, or Firm* — AMO Development, LLC.

(57) ABSTRACT

Systems and methods for fine-tuning refractive shapes for vision treatment are provided. Techniques encompass determining a variable index of refraction for a cornea of the eye, and determining the refractive treatment shape for the eye based on the variable index of refraction. Techniques also encompass determining a variable radius of curvature of an anterior surface of a cornea of the eye, and determining the refractive treatment shape for the eye based on the variable radius of curvature.

18 Claims, 6 Drawing Sheets

CORNEAL ABLATION DATA

SYSTEMS AND METHODS FOR FINE-TUNING REFRACTIVE SURGERY

CROSS-REFERENCES TO RELATED APPLICATIONS

This application is a nonprovisional of, and claims the benefit of priority to, U.S. Provisional Patent Application No. 60/953,425 filed Aug. 1, 2007, which is incorporated herein by reference for all purposes.

BACKGROUND OF THE INVENTION

Embodiments of the present invention relate the field of vision treatment, and in particular to systems and methods for fine-tuning ablation profiles and other treatment shapes.

Many current laser correction techniques are based on a nominal value that reflects a constant index of refraction of the corneal stroma. These techniques do not consider the variation that may exist in the refractive index of the corneal stroma. Known techniques are often based on a nominal value, which may be 1.376, for example. Moreover, many current approaches are based on or employ a nominal value that reflects a constant radius of curvature of the anterior surface of the cornea. This can cause up to about a 2% to 3% error in ablation depth, for example.

However, such estimations may not accurately represent the actual anatomy of the ocular system, or changes that may occur in the anatomy or the ablation process as the ablation process is carried out. Hence there is a need for systems and methods that consider a variation in the refractive index, which more closely approximates the ocular anatomy. Moreover, there is a need for systems and methods that consider a variation in the radius of curvature, which more closely approximates the ocular anatomy. Embodiments of the present invention provide solutions for at least some of these needs.

BRIEF SUMMARY OF THE INVENTION

Embodiments of the present invention provide techniques for fine-tuning ablation profiles for both conventional non-wavefront and wavefront-driven refractive surgery. These techniques can be implemented in a variety of laser and aberrometer devices, including without limitation the VISX WaveScan WaveFront System and STAR S4 Excimer Laser System, the Wavelight Alegretto and Tscherning-based aberrometer; the Alcon Ladarvision lasers and Ladarwave aberrometer; the Bausch and Lomb Zyoptix laser and related aberrometer, and the Zeiss laser and WASCA aberrometer.

Typically the index of refraction of the corneal stroma is not constant. For example, the index of refraction may change from about 1.38 at the anterior surface to about 1.373 at the posterior surface of the cornea. Advantageously, embodiments of the present invention encompass techniques that consider such a change in the refractive index. Accordingly, it is possible to obtain an improvement in the accuracy of an ablation profile or treatment shape. In some cases, this involves a consideration of high order aberrations. Moreover, typically the radius of curvature of the anterior surface of the cornea is not constant. Advantageously, embodiments of the present invention encompass techniques that consider a variable corneal radius of curvature.

Embodiments of the present invention encompass accurate techniques that take into account a change in refractive index of the corneal stroma. Embodiments of the present invention also encompass accurate techniques that take into account a customized radius of curvature of the anterior surface of the stroma. These techniques can be implemented in, for example, a VSS refractive treatment.

In one aspect, embodiments of the present invention encompass systems for determining a refractive treatment shape for an eye of a patient. Systems may include, for example, an input configured to receive a variable index of refraction for a cornea of the eye, and a processing module comprising a tangible medium embodying machine-readable code that determines the refractive treatment shape for the eye based on the variable index of refraction. In some cases, the refractive treatment shape can be configured to treat hyperopia or myopia. In some cases, the processing module can include a tangible medium embodying machine-readable code that determines the refractive treatment shape for the eye based on a Munnerlyn shape or a wavefront analysis of the eye. Optionally, systems may include an ablation system configured to apply the refractive treatment shape to the patient. The variable index of refraction can vary as a function of an ablation depth.

In some aspects, embodiments of the present invention encompass systems for determining a refractive treatment shape for an eye of a patient, such that the systems include an input configured to receive an instantaneous index of refraction for a cornea of the eye, and a processing module having a tangible medium embodying machine-readable code that determines the refractive treatment shape of a remaining ablation for the eye based on the instantaneous index of refraction. Systems may also include an ablation system configured to apply the refractive treatment shape to the patient. In some cases, systems include sensor or sensing assembly that detects the instantaneous index of refraction. The instantaneous index of refraction can vary as a function of an ablation depth.

In a further aspect, embodiments of the present invention encompass systems for determining a refractive treatment shape for an eye of a patient, such that a system may include an input configured to receive a variable radius of curvature of an anterior surface of a cornea of the eye, and a processing module with a tangible medium embodying machine-readable code that determines the refractive treatment shape for the eye based on the variable radius of curvature of the anterior surface. Systems may also have an ablation system configured to apply the refractive treatment shape to the patient. In some cases, the variable radius of curvature of the anterior surface of the eye is a function of a radius of curvature of a posterior surface of the cornea. In some cases, the variable radius of curvature of the anterior surface of the eye can vary as a function of an ablation depth.

In another aspect, embodiments of the present invention encompass systems for determining a refractive treatment shape for an eye of a patient, where a system can have an input configured to receive an instantaneous radius of curvature of an anterior surface of a cornea of the eye, and a processing module with a tangible medium embodying machine-readable code that determines the refractive treatment shape of a remaining ablation for the eye based on the instantaneous radius of curvature of the anterior surface of the cornea of the eye. Systems may also include an ablation system configured to apply the refractive treatment shape to the patient. In some cases, systems include a sensor or sensor assembly that detects the instantaneous radius of curvature of the anterior surface of the cornea of the eye. The instantaneous radius of curvature of the anterior surface of the eye can vary as a function of an ablation depth. The refractive treatment shape for the eye can be based on a Munnerlyn equation.

In yet another aspect, embodiments of the present invention encompass methods of determining a refractive treatment shape for an eye of a patient. Methods may include, for example, determining a variable index of refraction for a cornea of the eye, and determining the refractive treatment shape for the eye based on the variable index of refraction. In some cases, the step of determining the refractive treatment shape involves determining a refractive treatment shape of a remaining ablation for the eye based on the variable index of refraction. In some cases, the variable index of refraction for the cornea varies between an anterior portion of the cornea and a posterior portion of the cornea. In some cases, the variable index of refraction for the cornea varies across at least a portion of a corneal stroma. Relatedly, the variable index of refraction for the cornea can vary as a function of corneal stromal depth. The variable index of refraction for the cornea may vary as a linear function of corneal stromal depth. In some cases, the variable index of refraction for the cornea varies as a nonlinear function of corneal stromal depth. The refractive treatment shape can be configured to treat hyperopia. Relatedly, the refractive treatment shape can be configured to treat myopia. In some cases, the refractive treatment shape is determined based on a Munnerlyn shape. In some cases, the refractive treatment shape is determined based on a wavefront analysis of the eye. The variable index of refraction for the cornea of the eye may be determined following application of one or more ablation pulses to the eye. Optionally, the step of determining the variable index of refraction for a cornea of the eye can include determining an instantaneous variable index of refraction for the cornea following application of one or more ablation pulses to the eye, and the step of determining the refractive treatment shape can include determining a refractive treatment shape of a remaining ablation for the eye based on the instantaneous variable index of refraction. Methods may also involve applying the refractive treatment shape to the eye with an ablation system.

In another aspect, embodiments of the present invention encompass methods of determining a refractive treatment shape for an eye of a patient that include, for example, determining a variable radius of curvature of an anterior surface of a cornea of the eye, and determining the refractive treatment shape for the eye based on the variable radius of curvature. In some cases, the step of determining the refractive treatment shape involves determining a refractive treatment shape of a remaining ablation for the eye based on the variable radius of curvature. In some cases, the variable radius of curvature for the cornea of the eye is determined following application of one or more ablation pulses to the eye. Optionally, the step of determining the variable radius of curvature can include determining an instantaneous variable radius of curvature for the cornea following application of one or more ablation pulses to the eye, and the step of determining the refractive treatment shape can include determining a refractive treatment shape of a remaining ablation for the eye based on the instantaneous variable radius of curvature. Methods may also include applying the refractive treatment shape to the eye with an ablation system. In some cases, the variable radius of curvature of the anterior surface of the eye varies as a function of cornea thickness. In some cases, the variable radius of curvature of the anterior surface of the eye is a function of a radius of curvature of a posterior surface of the cornea. In some cases, the variable radius of curvature of the anterior surface of the eye varies as a function of an ablation depth. Optionally, the refractive treatment shape for the eye can be based on a Munnerlyn equation.

For a fuller understanding of the nature and advantages of the present invention, reference should be had to the ensuing detailed description taken in conjunction with the accompanying drawings.

DETAILED DESCRIPTION OF THE INVENTION

The present invention can be readily adapted for use with existing laser systems, wavefront measurement systems, and other optical measurement devices. Although the systems, software, and methods of the present invention are described primarily in the context of a laser eye surgery system, it should be understood the present invention may be adapted for use in alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy.

Figure 1:
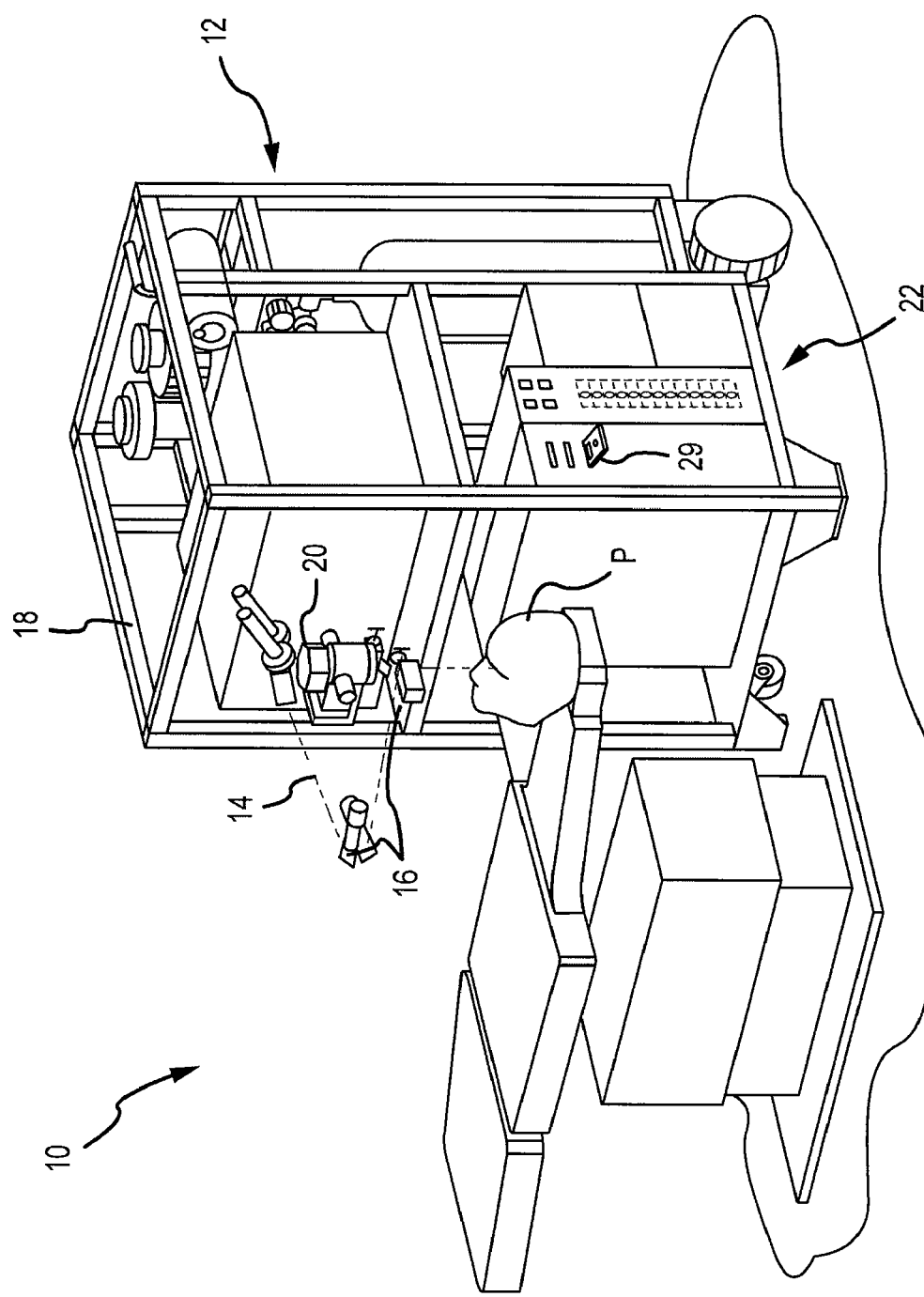
FIG. 1 illustrates a laser ablation system according to an embodiment of the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
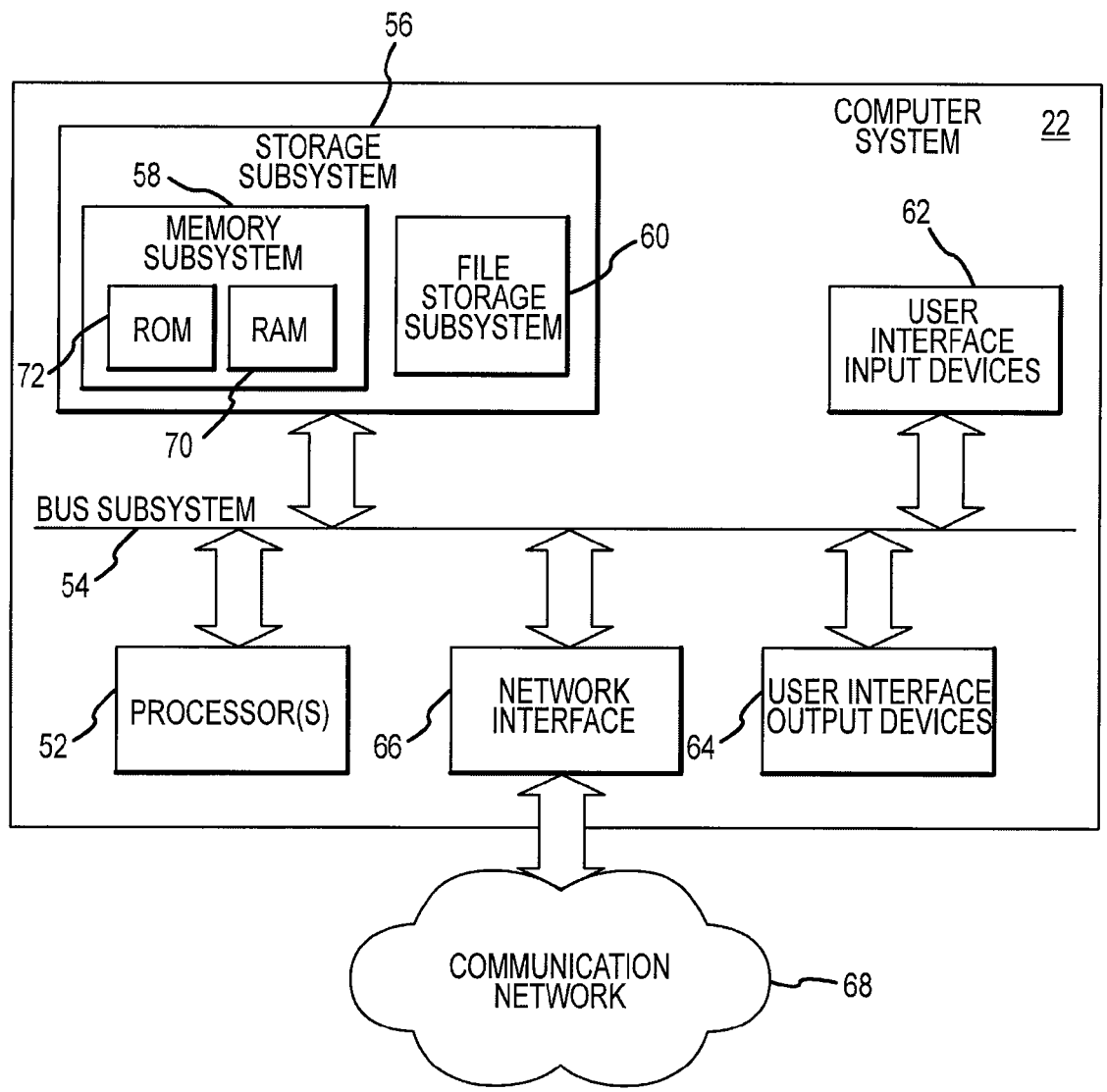
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
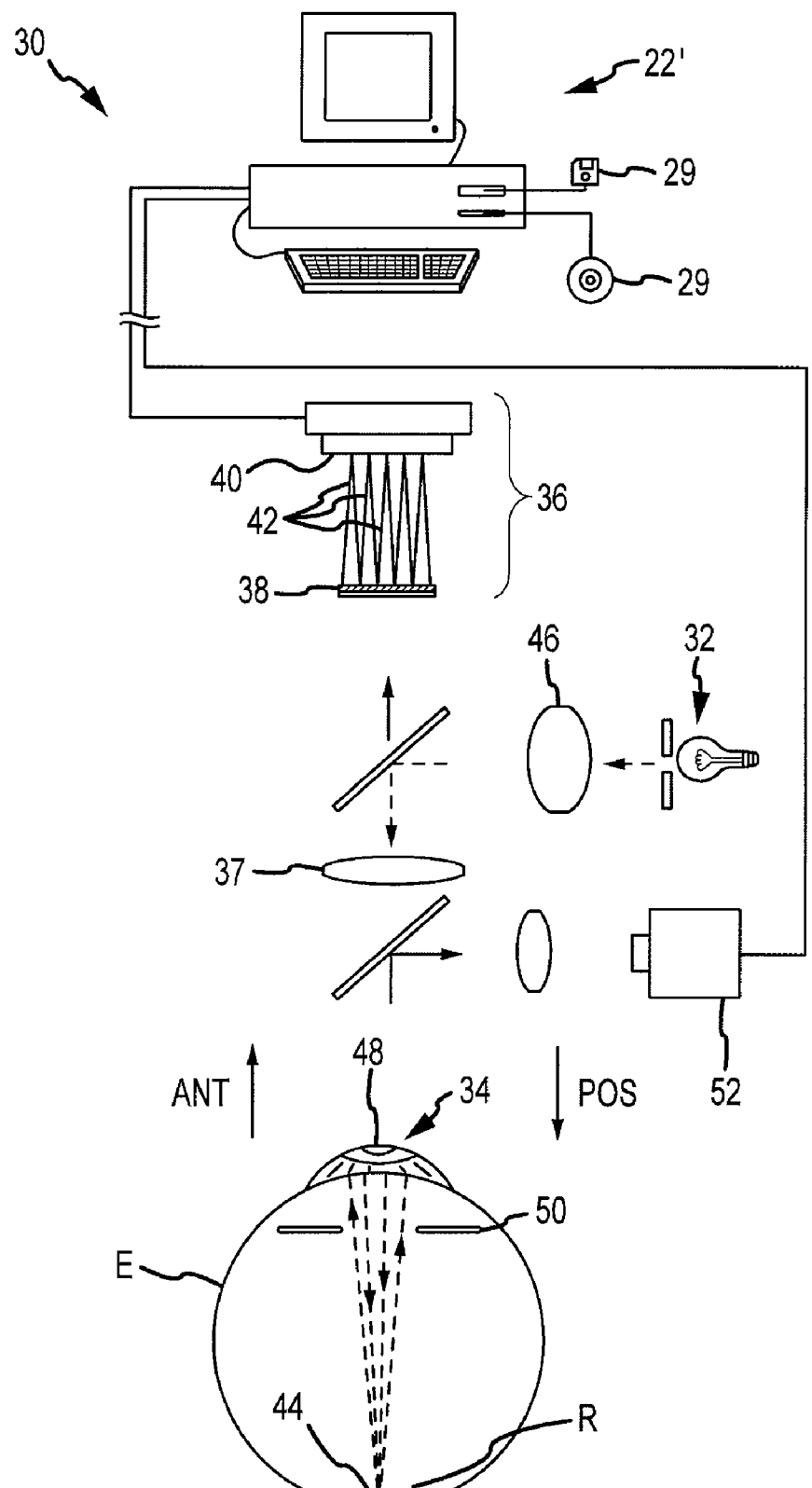
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
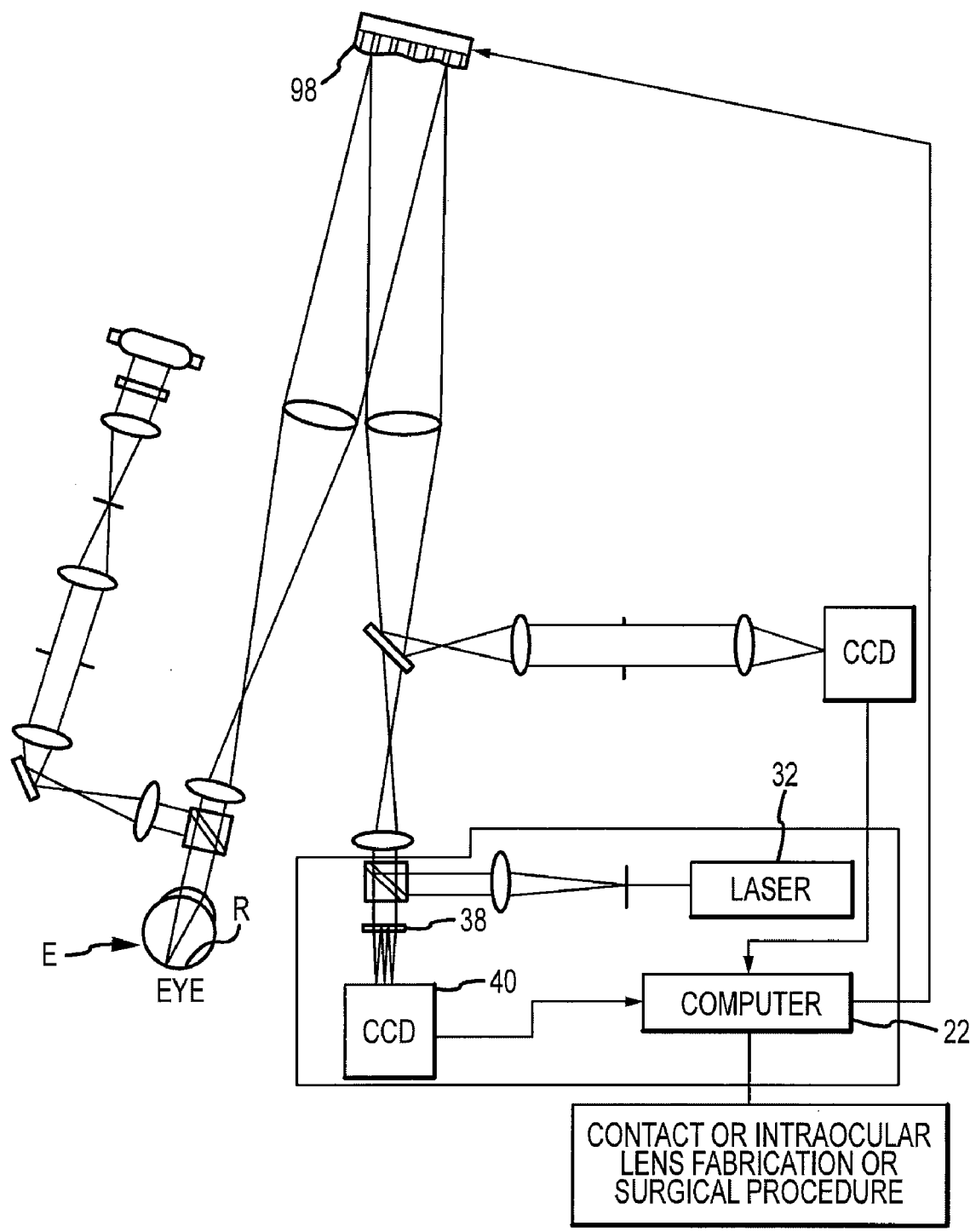
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from VISX, INCORPORATED of Santa Clara, Calif. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like.

Embodiments of the present invention encompass techniques that consider the index of refraction for corneal stroma as a function of depth or radial distance, and the radius of curvature variation as a laser ablates deeper and deeper tissue.

Using a Munnerlyn equation, it can be calculated that as the tissue is being ablated, each diopter of ablation has a smaller value of refractive index and larger value of the radius of curvature for myopia and a smaller value of the radius of curvature of the cornea for hyperopia, as the ablation goes deeper and deeper. In consequence, for a −6 D ablation, a 2% overcorrection can be estimated. For a +6 D ablation, a 2% undercorrection can be evaluated.

Excimer laser refractive surgery has been proven as a favorable vision correction means. It is often desirable to achieve a correction or treatment of the low order spherocylindrical error. Moreover, it is also desirable to achieve a favorable outcome of the refractive correction of ocular aberrations. Any small deviation may affect the final outcome of the surgery.

Embodiments of the present invention encompass techniques that can address factors which may affect a precise correction of low order aberrations or otherwise induce some high order aberrations, preventing a complete or desired correction of ocular aberrations. A methodology used for evaluating the possible error due to an imperfect system is described in G.-m. Dai et al. "System performance evaluation of refractive surgical lasers: a mathematical approach," Appl. Opt. 45, 2124-2134 (2006), which is incorporated herein by reference for all purposes.

Variable Index of Refraction of the Cornea

The refractive index may be dependent on the frequency of light. In some embodiments, only the indices at visible light are considered. In some embodiments, indices at other frequencies are considered. The refractive index of the corneal stroma may be assumed to be a constant by taking an average of the values of the anterior and posterior surfaces of the stroma. This is an approximation. The refractive index of the stroma may vary vertically and horizontally. Aspects of this variation are discussed in M. Dubbelman et al. "The shape of the aging human lens: curvature, equivalent refractive index and the lens paradox," Vis. Res. 41, 1867-1877 (2001), which is incorporated herein by reference for all purposes. The refractive index can be higher toward the periphery of the stroma, and lower toward the center of the stroma. Relatedly, the refractive index can be higher toward the anterior stroma, and lower toward the posterior stroma.

It is possible to denote n(h) as the refractive index of the stroma at the ablation depth h, and the refractive index of the stroma as $$n(h) = n_o + \delta h, \quad (1)$$

where the refractive index of the outermost layer of the stroma $n_0 = 1.38$ and the mean gradient index of the stroma $\delta = (1.373-1.38)/5.5 \times 10^{31\ 4} = -12.73$ m$^{-1}$. In Eq. (1), a nominal value of 550 μm for the thickness of the cornea can be assumed. For example, when the stroma is ablated for 50 μm, the refractive index is reduced from 1.38 to $1.38 - 12.73 \times 50 \times 10^{-6} = 1.379$. When the entire stroma of 550 μm is ablated, the refractive index can drop to 1.373.

In some embodiments, instead of using a nominal value of 1.376 for the refractive index of the stroma, it is possible to use Eq. (1) to represent the refractive index of the stroma as a function of the ablation depth h where $n_0$ is the refractive index of the stroma at the surface, and is 1.379. For surface ablations, such as LASEK and PRK, Eq. (1) can be used such that $n_0 = 1.39$ is the refractive index of the anterior surface of the stroma. When it is used for LASIK, $n_0$ may depend upon the thickness of the LASIK flap. For example, for normal flap thickness of 160 microns, $n_0$ can be 1.3770. For thin flaps of 110 microns that can be created with IntraLase femtosecond lasers, $n_0$ can be 1.3776.

Table 1 shows the ablation depth for every diopter of myopia and hyperopia for different levels of refractions with a 6 mm optical zone. Optionally, these values can be calculated using the Munnerlyn equation. Relatedly, Table 1 can provide the basis for an example for a deviation from a Munnerlyn equation on a per diopter situation. For a myopic ablation, the per diopter ablation depth becomes less deep as the ablation progresses. In comparison, for a hyperopic ablation, the per diopter ablation depth becomes deeper as the ablation continues. Hence, there can be a nonlinear relationship between the ablation depth and power, for example. According to some embodiments, the variable index of refraction for the cornea varies as a function of corneal stromal depth. In some cases, the function in Eq. (1) is linear. However, the per-diopter depth of ablation as a function of the ablation depth can be non-linear. Table 1 shows an ablation depth per diopter as a function of the sphere of myopia and hyperopia. An optical zone O=6 mm and the pre-surgery corneal radius of curvature $R_1$=7.8 mm are assumed. In some cases, techniques may involve ablation depth per partial diopter as a function of the sphere or myopia or hyperopia. Partial diopters can include half diopters, quarter diopters, and the like. In some cases, partial diopters can be considered as infinitesimally small or approaching zero, for example.

TABLE 1

| Sphere | | Myopia | | Hyperopia | |
| --- | --- | --- | --- | --- | --- |
| (D) | n | $R_1$ (mm) | Depth (μm) | $R_1$ (mm) | Depth (μm) |
| 1 | 1.3799 | 7.80 | 13.310 | 7.80 | 13.381 |
| 2 | 1.3797 | 7.96 | 13.248 | 7.64 | 13.459 |
| 3 | 1.3796 | 8.13 | 13.188 | 7.49 | 13.541 |
| 4 | 1.3794 | 8.31 | 13.130 | 7.35 | 13.625 |
| 5 | 1.3792 | 8.50 | 13.074 | 7.21 | 13.711 |
| 6 | 1.3791 | 8.69 | 13.019 | 7.07 | 13.800 |
| 7 | 1.3789 | 8.90 | 12.967 | 6.94 | 13.893 |
| 8 | 1.3787 | 9.11 | 12.917 | 6.82 | 13.988 |
| 9 | 1.3786 | 9.34 | 12.868 | 6.70 | 14.086 |
| 10 | 1.3784 | 9.57 | 12.821 | 6.58 | 14.187 |

Based on Table 1, it is apparent that for a myopia treatment, the ablation depth can change from about 13.31 microns for the first diopter to about 12.82 microns for the tenth diopter. Similarly, for a hyperopia treatment, the ablation depth can change from about 13.38 microns for the first diopter to about 14.19 microns for the tenth diopter.

As an exemplary illustration, for a −6 D myopic eye it is possible to calculate the deviation of true depth using variable refractive index as compared to using the mean refractive index for O=6 mm optical zone. Consider for example that a depth per diopter myopia is 13.43 μm so the total depth for a −6 D eye is 13.43×6=80.58 μm. To calculate the depth with the variable refractive index, adding the first six values in Table 1 for myopia, it is possible to obtain 78.97 μm. Therefore, the fixed refractive index model over-ablates a −6 D myopic eye by 80.58−78.97=1.611 μm. This is a 2% overcorrection.

As an ablation continues, the index of refraction of the resulting anterior stromal layer can change. Hence, a variable index of refraction can vary as a function of ablation depth. In some cases, embodiments of the present invention encompass techniques that incorporate a precalculated variable index of refraction. In some cases, embodiments encompass techniques that incorporate an ongoing or instantaneous refinement of the variable index of refraction calculation. In other words, a variable index determination can be used to drive a treatment from the start, and can also be used to form the basis for providing ongoing refinement of a treatment according to a closed-loop process. For example, a method of determining a refractive treatment shape can include determining an instantaneous index of refraction at one or more times during an ablation treatment, and determining or refining the refractive treatment shape based on the instantaneous index of refraction. Optionally, a method of determining a refractive treatment shape can include determining a variable index of refraction, and determining the refractive treatment shape of the remaining ablation for the eye based on the variable index of refraction. As the ablation progresses, the index of refraction can change as additional material is ablated.

In an open loop approach, a variable index of refraction can be based on a precalculated or predicted value. For example, a look-up table can be constructed such that the depth of the ablation profile can be found based on the refraction of the eye. Optionally, an infinitesimally thin profile can be constructed based upon the Munnerlyn equation or the wavefront-driven parabolic shape and an integration can be performed over the refraction of the eye when determining a final ablation profile. In a closed loop approach, an index of refraction can be monitored in real time during an ablation procedure, and ablation treatment parameters can be adjusted or refined based on the instantaneous refractive index or refractive index change. In some cases, the index of refraction can be measured following the application of one or more ablation pulses applied to the eye. The residual ablation profile can be determined based on the ablated profile and the instantaneous refractive index such that the final ablated profile when the ablation is complete optimally matches the planned ablation profile.

The depth of an ablation and the shape of tissue removed can vary based on the variable index of refraction. Variable index of refractions may vary between different patients. Embodiments disclosed herein provide tissue refractive index measurement and ablation systems suitable for integration with known laser eye surgery systems. Embodiments also encompass techniques that provide diagnostic information before, and/or feedback information during, a corneal resculpting procedure. Information regarding the index of refraction of the cornea or components of the cornea can be used to establish or modify a resculpting laser energy pattern for a corneal tissue surface.

Embodiments encompass systems and methods for measuring or detecting the index of refraction of a corneal or stromal tissue using, for example, a Scheimflug imaging technique. M. Dubbleman et al. discuss a method for determining the refractive index of the crystalline lens in "The shape of the aging human lens: curvature, equivalent refractive index and the lens paradox," Vis. Res. 41, 1867-1877 (2001), the entirety of which is incorporated herein by reference for all purposes. Systems may include a processor coupled with, in communication with, or otherwise configured to receive information from the sensor, whereby the processor can generate a refractive index signal indicating the refractive index of the tissue. Relatedly, embodiments encompass systems and methods for resculpting a corneal tissue of an eye. Systems may include an apparatus that directs a pattern of light energy from a laser under the direction of a processor to effect a desired change in an optical characteristic of the eye, and an adjustment module of a system processor can vary the pattern in response to the index of refraction information from a sensor.

In some cases, embodiments encompass compensation techniques for use in a procedure for resculpting a corneal tissue of an eye. A resculpting procedure can selectively direct a pattern of laser energy toward the eye to effect a predetermined change in an optical characteristic of the eye. A compensation method may include sensing or detecting a refractive index of the corneal or stromal tissue of the eye, and adjusting the pattern of laser energy in response to the sensed refractive index. An ablation energy delivery system can be coupled to a processor, the delivery system can direct an ablative energy toward the tissue, and the processor can vary the ablative energy in response to a refractive index signal. The tissue will typically include a corneal tissue of an eye, and the delivery system may include an optical delivery system transmitting photoablative laser energy toward the corneal tissue so as to selectively alter an optical characteristic of the eye. The processor may vary a quantity of change in the optical characteristic of the eye in response to the refractive index signal. For example, the processor may vary a diopter value of the resculpting procedure in response to the index of refraction. Alternatively, the processor may vary the shape of the ablation by altering the ablative energy pattern so as to compensate for local differences in refractive index across the target region of the corneal tissue. In some embodiments, an output device coupled to the processor may show a display in response to the index of refraction signal.

Systems and methods for sculpting of a corneal tissue of an eye to effect a desired change in an optical property are also provided herein. Such techniques can include sensing or detecting an index of refraction of a stromal tissue of the eye, and determining a desired change in shape of the eye in response to the index of refraction, and in response to the desired change in optical property. A pattern of laser energy can be planned for directing toward the corneal tissue, so as to effect the determined change in shape. A desired change in optical quality can be determined while the tissue has a initial index of refraction, or a subsequent index of refraction following or during an ablation or resculpting step. The change in optical quality may be determined using any of a variety of standard vision diagnostic systems. Wavefront sensor systems now being developed may also be beneficial for determining a desired change in an optical property, and still further alternative topography and/or tomography systems may also be used. Regardless, rather than simply determining the desired change in shape of the eye from such measurements alone, the desired sculpting or ablation shape can also be based in part on the index of refraction of the eye.

An exemplary method for performing a refractive index compensated photorefractive ablation may be initiated using a predetermined ablation pattern assuming a standard ablation rate. A sensor can be used to determine or evaluate the refractive index of stromal tissue of the eye. The standard ablation rate can be adjusted based on the refractive index, and the adjusted ablation rate can be part of a treatment pattern of ablation energy directed toward the tissue so as to effect the desired change in optical characteristics of eye. The treatment pattern, can include parameters such as the size, location, and/or number of laser pulses directed toward some or all of the treatment region of the eye. One or more of these parameters can be set or adjusted based on the refractive index. In some cases, an algorithm used to calculate a shot pattern so as to effect a desired change in corneal shape may incorporate adjusted ablation rates appropriate for a varying index of refraction.

As noted above, a refractive index can vary vertically based on stromal depth. A refractive index can also vary horizontally based on a function of radial distance from a central portion of the stroma. Radial dependency of the refractive index can characterize a stroma that has a lower index of refraction in a central portion of the stroma. In some cases, radial dependency can be characterized with the following formula: $n(r)=n_0+\lambda r$, where r represents the radial distance from a central portion of the stroma, and X represents the rate of change of the refractive index radially. Thus, it is possible to denote n(r) as the refractive index of the stroma at the radial distance r, where the refractive index of a central portion of the stroma is $n_0$, which can depend on the ablation depth. On the anterior surface of the cornea, it is about 1.38. On the anterior surface of the stroma, it is about 1.379. On the posterior surface of the stroma, it is about 1.373.

In some embodiments, techniques involve determining the variability of a refractive index of a patient, and determining a refractive treatment shape based on that variability. These approaches can be used to determine a treatment shape based on modification of a Munnerlyn shape. Optionally, these approaches can be used to determine a treatment shape based on a wavefront analysis.

Variable Corneal Radius of Curvature

In one approximation, the corneal radius of curvature can be considered as a constant. Some equations, such as the Munnerlyn equation, can incorporate this assumption. A relationship between the radius of curvature of the anterior surface of the cornea $R_1$ and the keratometry or keratometric power F can be expressed by $$R_1 = \frac{(n-1)[R_2 + (n-n_2)d]}{R_2 F + (n-n_2)(1+Fd)}, \qquad (2)$$

where n and $n_2$ are the refractive indices of the anterior and posterior surfaces of the stroma (or cornea), respectively, d is the cornea thickness or pachymetry, and $R_2$ is the radius of curvature of the posterior surface of the cornea. Because the values of d and $R_2$ typically vary from eye to eye, the calculated $R_1$ can also vary.

Figure 4A:
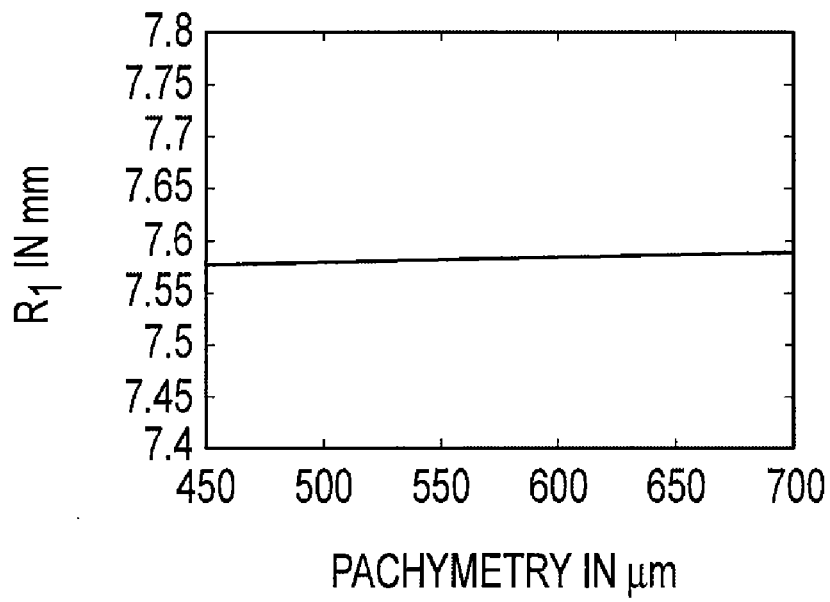
FIGS. 4A and 4B show aspects of an embodiment of the present invention.
Figure 4B:
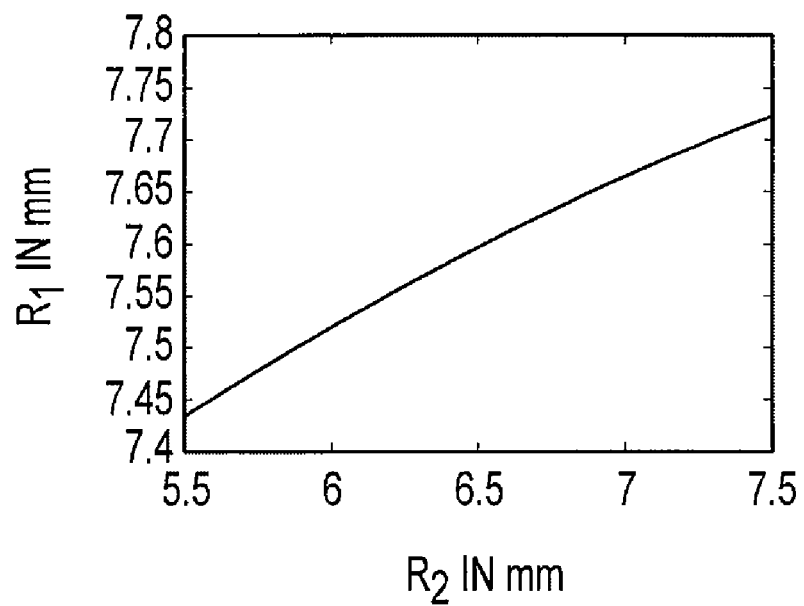

FIG. 4A illustrates a radius of curvature of the anterior surface of the cornea as a function of pachymetry or cornea thickness ($R_2$=6.4 mm). This figure shows the variability for the calculation of the radius of curvature of the anterior surface of the cornea as a function of the pachymetry, according to some embodiments. FIG. 4B illustrates a radius of curvature of the anterior surface of the cornea as a function of the radius of curvature of the posterior surface of the cornea (d=550 μm). Refractive indices n=1.3765 and $n_2$=1.336 are assumed. These figures show the variability for the calculation of the radius of curvature of the anterior surface of the cornea as a function of the radius of curvature of the posterior surface of the cornea, according to some embodiments. It is quite clear that the variability of $R_2$ gives the variability of $R_1$.

As an exemplary illustration, it is possible to calculate the deviation of the tissue ablation depth for a +1 D hyperopic eye using a 6 mm optical zone, when the radius of curvatures of the anterior and posterior surfaces of the cornea are taken as 6.4 mm and 7.5 mm, respectively. The keratometry and pachymetry are assumed to be 45 D and 550 μm, respectively.

From Eq. (2), for $R_2$=6.4 mm, F=45 D, and d=550 μm, it is possible to obtain $R_1$=(1.3765−1)×[0.0064+(1.3765−1.336)×0.00055]/[0.0064×45+(1.3765−1.336)×(1+45×0.00055)]m=7.34 mm. Similarly, for $R_2$=7.5 mm, it is possible to obtain $R_1$=7.47 mm. Substituting the two values of $R_1$ into the Munnerlyn equation Eq. (4), it is possible to obtain the depths as 13.73 μm and 13.66 μm, respectively. This example shows that a variability of about 20% on the value of $R_2$ can lead to about 0.5% mis-correction on the ablation profile.

Munnerlyn equations for myopia [Eq. (3)], and for hyperopia [Eq. (4)] can be expressed as follows.

$$l(r) = \sqrt{R_1^2 - r^2} - \sqrt{\left[\frac{(n-1)R_1}{n-1+SR_1}\right]^2 - r^2} + \sqrt{\left[\frac{(n-1)R_1}{n-1+SR_1}\right]^2 - (O/2)^2} - \sqrt{R_1^2 - (O/2)^2} \quad (3)$$

$$l(r) = \sqrt{R_1^2 - r^2} - R_1 + \frac{(n-1)R_1}{n-1+SR_1} - \sqrt{\left[\frac{(n-1)R_1}{n-1+SR_1}\right] - r^2} \quad (4)$$

Accordingly, embodiments of the present invention encompass techniques where an anterior radius of curvature can be incorporated into a Munnerlyn equation. Anterior optical surfaces may vary from person to person, and ablations may effect an anterior surface feature.

According to some embodiments, as the ablation progresses, the corneal radius of curvature can change. For example, as the ablation continues in a myopia treatment, the radius of curvature of the anterior cornea can become larger and larger. Relatedly, as the ablation continues in a hyperopia treatment, the radius of curvature of the anterior cornea can become smaller and smaller. Hence, a variable radius of curvature of the anterior surface of the eye can vary as a function of the ablation depth. Accordingly, embodiments of the present invention encompass techniques that incorporate ongoing or instantaneous refinement of the variable radius of curvature of the anterior surface calculation. In other words, a variable radius of curvature determination can be used to drive a treatment from the start, and can also be used to form the basis for providing ongoing refinement of a treatment according to a closed-loop process. For example, a method of determining a refractive treatment shape can include determining an instantaneous radius of curvature of the anterior surface at one or more times during an ablation treatment, and determining or refining the refractive treatment shape based on the instantaneous radius of curvature of the anterior surface. Optionally, a method of determining a refractive treatment shape can include determining a variable radius of curvature of the anterior surface, and determining the refractive treatment shape of the remaining ablation for the eye based on the variable radius of curvature of the anterior surface. As the ablation progresses, the radius of curvature of the anterior surface can change or vary as additional material is ablated. Thus, embodiments of the present invention encompass techniques for determining a refractive treatment shape that include determining the instantaneous keratometry as the ablation continues, and determining the refractive treatment shape for the remaining ablation based on the instantaneous keratometry.

As an ablation continues, the anterior corneal radius of curvature can change. Hence, a variable index of refraction can vary as a function of the anterior corneal radius of curvature. In some cases, embodiments of the present invention encompass techniques that incorporate a precalculated variable anterior corneal radius of curvature. In some cases, embodiments encompass techniques that incorporate an ongoing or instantaneous refinement of the variable anterior corneal radius of curvature calculation. In other words, a variable anterior corneal radius of curvature determination can be used to drive a treatment from the start, and can also be used to form the basis for providing ongoing refinement of a treatment according to a closed-loop process. For example, a method of determining a refractive treatment shape can include determining an instantaneous anterior corneal radius of curvature at one or more times during an ablation treatment, and determining or refining the refractive treatment shape based on the instantaneous anterior corneal radius of curvature. Optionally, a method of determining a refractive treatment shape can include determining a variable anterior corneal radius of curvature, and determining the refractive treatment shape of the remaining ablation for the eye based on the variable anterior corneal radius of curvature. As the ablation progresses, the anterior corneal radius of curvature can change as additional material is ablated.

In an open loop approach, a variable anterior corneal radius of curvature can be based on a precalculated or predicted value. For example, this value can be based on the keratometry measurements of the eye. Optionally, an infinitesimally thin profile can be constructed based upon the Munnerlyn equation or the wavefront-driven parabolic shape and an integration can be performed over the refraction of the eye to determine a final ablation profile. In a closed loop approach, an anterior corneal radius of curvature can be monitored in real time during an ablation procedure, and ablation treatment parameters can be adjusted or refined based on the instantaneous anterior corneal radius of curvature or anterior corneal radius of curvature change. In some cases, the anterior corneal radius of curvature can be measured following the application of one or more ablation pulses applied to the eye.

The depth of an ablation and the shape of tissue removed can vary based on the variable anterior corneal radius of curvature. Variable anterior corneal radius of curvatures may vary between different patients. Embodiments disclosed herein provide tissue radius of curvature measurement and ablation systems suitable for integration with known laser eye surgery systems. Embodiments also encompass techniques that provide diagnostic information before, and/or feedback information during, a corneal resculpting procedure. Information regarding the anterior corneal radius of curvature can be used to establish or modify a resculpting laser energy pattern for a corneal tissue surface.

Embodiments encompass systems and methods for measuring or detecting the anterior corneal radius of curvature. Systems may include a processor coupled with, in communication with, or otherwise configured to receive information from the sensor, whereby the processor can generate an anterior corneal radius of curvature signal indicating the anterior corneal radius of curvature. Relatedly, embodiments encompass systems and methods for resculpting a corneal tissue of an eye. Systems may include an apparatus that directs a pattern of light energy from a laser under the direction of a processor to effect a desired change in an optical characteristic of the eye, and an adjustment module of a system processor can vary the pattern in response to the anterior corneal radius of curvature information from a sensor.

In some cases, embodiments encompass compensation techniques for use in a procedure for resculpting a corneal tissue of an eye. A resculpting procedure can selectively direct a pattern of laser energy toward the eye to effect a predetermined change in an optical characteristic of the eye. A compensation method may include sensing or detecting an anterior corneal radius of curvature, and adjusting the pattern of laser energy in response to the sensed anterior corneal radius of curvature. An ablation energy delivery system can be coupled to a processor, the delivery system can direct an ablative energy toward the tissue, and the processor can vary the ablative energy in response to an anterior corneal radius of curvature signal. The tissue will typically include a corneal tissue of an eye, and the delivery system may include an optical delivery system transmitting photoablative laser energy toward the corneal tissue so as to selectively alter an optical characteristic of the eye. The processor may vary a quantity of change in the optical characteristic of the eye in response to the anterior corneal radius of curvature signal. For example, the processor may vary a diopter value of the resculpting procedure in response to the anterior corneal radius of curvature. Alternatively, the processor may vary the shape of the ablation by altering the ablative energy pattern so as to compensate for local differences in anterior corneal radius of curvature across the target region of the corneal tissue. In some embodiments, an output device coupled to the processor may show a display in response to the anterior corneal radius of curvature signal.

Systems and methods for sculpting of a corneal tissue of an eye to effect a desired change in an optical property are also provided herein. Such techniques can include sensing or detecting an anterior corneal radius of curvature, and determining a desired change in shape of the eye in response to the anterior corneal radius of curvature, and in response to the desired change in optical property. A pattern of laser energy can be planned for directing toward the corneal tissue, so at to effect the determined change in shape. A desired change in optical quality can be determined while the tissue has a initial anterior corneal radius of curvature, or a subsequent anterior corneal radius of curvature following or during an ablation or resculpting step. The change in optical quality may be determined using any of a variety of standard vision diagnostic systems. Wavefront sensor systems now being developed may also be beneficial for determining a desired change in an optical property, and still further alternative topography and/or tomography systems may also be used. Regardless, rather than simply determining the desired change in shape of the eye from such measurements alone, the desired sculpting or ablation shape can also be based in part on the anterior corneal radius of curvature.

An exemplary method for performing an anterior corneal radius of curvature compensated photorefractive ablation may be initiated using a predetermined ablation pattern assuming a standard ablation rate. A sensor can be used to determine or evaluate the anterior corneal radius of curvature. The standard ablation rate can be adjusted based on the anterior corneal radius of curvature, and the adjusted ablation rate can be part of a treatment pattern of ablation energy directed toward the tissue so as to effect the desired change in optical characteristics of eye. The treatment pattern, can include parameters such as the size, location, and/or number of laser pulses directed toward some or all of the treatment region of the eye. One or more of these parameters can be set or adjusted based on the anterior corneal radius of curvature. In some cases, an algorithm used to calculate a shot pattern so as to effect a desired change in corneal shape may incorporate adjusted ablation rates appropriate for a varying anterior corneal radius of curvature.

Embodiments of the present invention may involve fine-tuning techniques that incorporate wavefront and topographic features of an optical system. Exemplary approaches for determining shapes and features of the topography of a corneal of the eye are discussed in, for example, U.S. patent application Ser. Nos. 11/769,054 and 12/119,293 filed Jun. 27, 2007 and May 12, 2008, respectively, which are incorporated herein by reference for all purposes.

Compensation of Corneal Biomechanics and Healing

Techniques that involve cutting a flap with a microkeratome may cause a change of the high order aberrations. In some laser ablations, an increase of the high order aberrations can be dominated by the spherical aberrations. In general, when the pre-operative high order root mean square (RMS) error of the aberrations is low, ocular aberrations can tend to increase after surgery. On the other hand, when the pre-operative high order RMS error is high, ocular aberrations can tend to decrease. The increase of the spherical aberration post-surgery may not be all due to the biomechanics and healing, neglect of some of the effects discussed in this section may also cause an increase in spherical aberrations.

To compensate for the induction of ocular aberrations due to biomechanics and healing, mechanical and optical models have been proposed. For example, one way to account for the induction of ocular aberrations is to treat the biomechanical and healing effects as a low pass filtering process. When a flap is laid onto an ablated structure, some of the sharper, or higher spatial frequency, features can be smoothed. Similarly, when the ablated cornea heals, some of the smaller structures, whether it is due to the flap cut or due to the gaps between the laser pulses, can also be smoothed out.

Another approach, which can be useful in addressing the effect of a flap cut, for example, is to use mechanical models. Before the LASIK flap is cut, the tension of the lamellae is maintained between the interlamellar crosslinking, and the corneal internal fluid and intraocular pressures. After the flap is cut, the lamellar segments at the edge of the cut lose the tension, hence making the peripheral cornea to expand. This in turn can increase the interlamellar spacing, causing the edge of the cut to bulge and the central ablation area to flatten. After the flap is put back, the lost tension at the edge of the flap may not be able to recover. Therefore, the deformation of the cornea due to the flap cut may remain. Optically, this can create a phase advance at the center of the cut and a phase lag at the periphery, or the induction of a positive spherical aberration. With modeling, such as with finite element method, for example, a prediction of the corneal surface deformation after flap cut is possible.

Determination of Treatment Shape

In some embodiments, systems and methods may involve producing a treatment shape in a variety of steps. For example, an optical region shape can be determined, either by Munnerlyn equations or wavefront techniques. In some cases, aspects of the shape can be smoothed by pixel averaging, or by spatial averaging of depth.

Once the desired ablation shape has been determined, a next step is to define the parameters of the actual laser ablation required to administer the treatment ablation profile. A particularly useful way of determining these parameters is by using an ablation equation, such as the one shown below.

$$AblationShape = \sum_{n=1}^{TotalPulses} (PulseShape_n \otimes Position_n)$$

In brief, this equation is based on the principle that a treatment ablation is the sum of each of the individual laser pulses. This equation has been empirically verified on a variety of materials including plastic, and bovine, porcine, and human corneal tissue.

In this equation, the AblationShape variable represents the desired ablation shape. In this sense, it is a known variable. The target shape can be, for example, a simple sphere, an ellipse, a cylinder for treating myopia or hyperopia, or even a saddle for treating mixed astigmatism. The target shape can be any arbitrary shape, such as the map from a wavefront type device or any other topography system.

Figure 5:
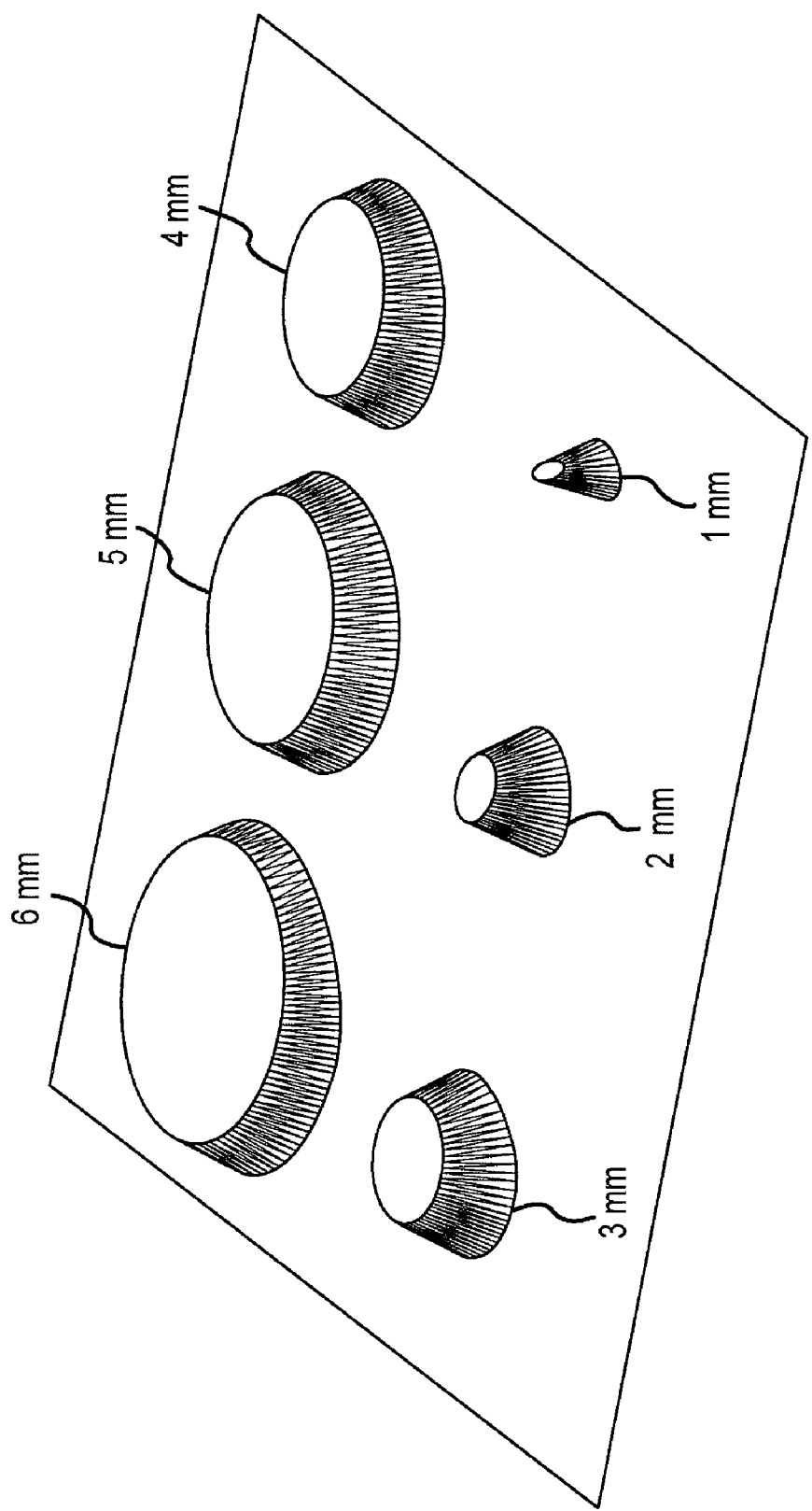
FIG. 5 shows corneal ablation data according to embodiments of the present invention.

The PulseShape variable, which is also a known variable, represents the ablation shape of each laser pulse size to be used. The PulseShape typically varies for different ablated materials, such as plastic, animal cornea, or human cornea. The PulseShape also typically varies for each laser pulse diameter. An example of this type of ablation data is shown in FIG. 5. This figure shows different shapes of craters expected from a single laser pulse. There is a unique description for every unique pulse shape or size to be used. By systematically measuring the shape which each laser pulse ablates onto a specific target material, it is possible to generate such basis data for a variety of materials, such as tissue or plastic. For a given material, at a given diameter, the shape is generally consistent from laser system to laser system.

A fixed spot laser may have only one description, while a variable spot laser could have as many as desired. There is no requirement that the crater shape be flat, round, or symmetric. As long as it can be described mathematically or with an array of data, it can be incorporated in the equation.

In order to create the ablated surface, it is useful to determine the locations where each of the laser pulses will be applied. The Position variable, which represents the exact position of every laser pulse, is an unknown variable. This variable is calculated by solving the ablation equation. Put another way, the output is a set of instructions for creating the target ablation shape using the laser pulses. This is sometimes called a treatment table. The treatment table consists of a list of individual pulses, each containing the size and offset, or position, to be used for that pulse. When the laser fires according to the instructions in the treatment table, the target shape will be created.

The target ablation shape is a theoretical construct; it is a mathematically perfect representation of a desired ablation outcome. Put another way, while the application of thousands of specifically placed brief laser pulses can create an actual ablation shape that approaches the ideal target ablation shape, in the end it is still an approximation thereof.

Therefore, solving for the Position variable can allow for the formulation of a corresponding ablation shape that approaches the target ablation shape as closely as possible. In this way each of the thousands of pulse positions are individually determined so as to minimize the difference between the ideal target ablation shape and the actual resulting ablation shape. In a system for ablating tissue using a scanning laser, a presently preferred computational technique for achieving this goal employs simulated annealing.

Other mathematical approaches include, for example, the SALSA Algorithm. SALSA is an acronym for Simulated Annealing Least Squares Algorithm. It is an algorithm that solves an equation having over 10,000 unknowns. The algorithm finds the best solution by selecting: the number of pulses, the size of each pulse, and the location of each pulse. It is an exact algorithm, and makes no statistical assumptions.

Simulated Annealing is a recent, proven method to solve otherwise intractable problems, and may be used to solve the ablation equation discussed above. This is more fully described in PCT Application No. PCT/US01/08337, filed Mar. 14, 2001, the entire disclose of which is incorporated herein by reference. See also W. H. Press et al., "Numerical Recipes in C" $2^{nd}$ Ed., Cambridge University Press, pp. 444-455 (1992). This approach is also further discussed in co-pending U.S. patent application Ser. No. 09/805,737, the entire disclosure of which is incorporated herein by reference.

Simulated annealing is a method used for minimizing (or maximizing) the parameters of a function. It is particularly suited to problems with very large, poorly behaved function spaces. Simulated annealing can be applied in the same way regardless of how many dimensions are present in the search space. It can be used to optimize any conditions that can be expressed numerically, and it does not require a derivative. It can also provide an accurate overall minimum despite local minima in the search space, for example.

The methods and apparatuses of the present invention may be provided in one or more kits for such use. The kits may comprise a system for profiling an optical surface, such as an optical surface of an eye, and instructions for use. Optionally, such kits may further include any of the other system components described in relation to the present invention and any other materials or items relevant to the present invention. The instructions for use can set forth any of the methods as described above.

Each of the above calculations or operations may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

While the above provides a full and complete disclosure of the preferred embodiments of the present invention, various modifications, alternate constructions and equivalents may be employed as desired. Therefore, the above description and illustrations should not be construed as limiting the invention, which can be defined by the appended claims.

What is claimed is:

1. A system for determining a refractive treatment shape for an eye of a patient, the system comprising:
    an input configured to receive a function representing a variable index of refraction for a cornea of the eye, wherein the function comprises an index of refraction term n(h) that varies according to a corneal stromal depth term h; and
    a processing module comprising a tangible medium embodying machine-readable code that determines the refractive treatment shape for the eye, the processing module receiving the function representing the variable index of refraction to determine the refractive treatment shape of the eye.

2. The system according to claim 1, wherein the refractive treatment shape is configured to treat hyperopia or myopia.

3. The system according to claim 1, wherein the processing module comprises a tangible medium embodying machine-readable code that determines the refractive treatment shape for the eye based on a Munnerlyn shape or a wavefront analysis of the eye.

4. The system according to claim 1, further comprising an ablation system configured to apply the refractive treatment shape to the patient.

5. The system according to claim 1, wherein the function representing the variable index of refraction for the cornea varies between an anterior portion of the cornea and a posterior portion of the cornea.

6. The system according to claim 1, wherein the function representing the variable index of refraction for the cornea varies as a linear function of corneal stromal depth.

7. The system according to claim 1, wherein the function representing the variable index of refraction for the cornea varies as a nonlinear function of corneal stromal depth.

8. A method of determining a refractive treatment shape for an eye of a patient, the method comprising:

determining a function representing a variable index of refraction for a cornea of the eye, wherein the function comprises an index of refraction term n(h) that varies according to a corneal stromal depth term h; and using a processing module comprising a tangible medium embodying machine-readable code to determine the refractive treatment shape for the eye based on the function representing the variable index of refraction.

9. The method according to claim 8, wherein determining the refractive treatment shape comprises determining a refractive treatment shape of a remaining ablation for the eye based on the function representing the variable index of refraction.

10. The method according to claim 8, wherein the function representing the variable index of refraction for the cornea varies between an anterior portion of the cornea and a posterior portion of the cornea.

11. The method according to claim 8, wherein the function representing the variable index of refraction for the cornea varies as a linear function of corneal stromal depth.

12. The method according to claim 8, wherein the function representing the variable index of refraction for the cornea varies as a nonlinear function of corneal stromal depth.

13. The method according to claim 8, wherein the refractive treatment shape is configured to treat hyperopia.

14. The method according to claim 8, wherein the refractive treatment shape is configured to treat myopia.

15. The method according to claim 8, wherein the refractive treatment shape is determined based on a Munnerlyn shape.

16. The method according to claim 8, wherein the refractive treatment shape is determined based on a wavefront analysis of the eye.

17. The method according to claim 8, wherein the the function representing variable index of refraction for the cornea of the eye is determined following application of one or more ablation pulses to the eye.

18. The method according to claim 8, further comprising applying the refractive treatment shape to the eye with an ablation system.

* * * * *